(12) United States Patent
Rudser et al.

(10) Patent No.: US 9,782,598 B2
(45) Date of Patent: Oct. 10, 2017

(54) PASS-THROUGH ASSEMBLY

(71) Applicant: HeartWare, Inc., Miami Lakes, FL (US)

(72) Inventors: John Rudser, Miami, FL (US); Alfredo Garcell, Melbourne, FL (US)

(73) Assignee: HeartWare, Inc., Miami Lakes, FL (US)

( * ) Notice: Subject to any disclaimer, the term of this patent is extended or adjusted under 35 U.S.C. 154(b) by 0 days.

(21) Appl. No.: 14/915,083

(22) PCT Filed: Aug. 28, 2014

(86) PCT No.: PCT/US2014/053186
§ 371 (c)(1),
(2) Date: Feb. 26, 2016

(87) PCT Pub. No.: WO2015/031630
PCT Pub. Date: Mar. 5, 2015

(65) Prior Publication Data
US 2016/0206888 A1 Jul. 21, 2016

Related U.S. Application Data

(60) Provisional application No. 61/871,046, filed on Aug. 28, 2013.

(51) Int. Cl.
*A61N 1/375* (2006.01)
*A61M 1/12* (2006.01)
(Continued)

(52) U.S. Cl.
CPC ......... *A61N 1/3754* (2013.01); *A61M 1/1008* (2014.02); *A61M 1/122* (2014.02);
(Continued)

(58) Field of Classification Search
CPC ... A61N 1/3754; A61M 1/1008; A61M 1/122; A61M 1/127; A61M 30/1011
(Continued)

(56) References Cited

U.S. PATENT DOCUMENTS

| 5,324,312 | A  |   | 6/1994  | Stokes et al. |                      |
|-----------|----|---|---------|---------------|----------------------|
| 5,493,073 | A  | * | 2/1996  | Honkomp       | H01B 17/305          |
|           |    |   |         |               | 174/152 GM           |
| 5,905,627 | A  | * | 5/1999  | Brendel       | H01G 4/35            |
|           |    |   |         |               | 333/182              |
| 6,609,029 | B1 |   | 8/2003  | Mann et al.   |                      |
| 7,442,081 | B2 | * | 10/2008 | Burke         | B29C 45/14639        |
|           |    |   |         |               | 439/589              |
| 7,500,793 | B2 | * | 3/2009  | Patel         | G02B 6/3833          |
|           |    |   |         |               | 385/128              |
| 7,901,247 | B2 | * | 3/2011  | Ring          | H01R 13/405          |
|           |    |   |         |               | 439/606              |
| 8,943,686 | B2 | * | 2/2015  | Hartford      | H01R 13/53           |
|           |    |   |         |               | 148/22               |
| 8,969,741 | B2 | * | 3/2015  | Aldrich       | 174/650              |

(Continued)

FOREIGN PATENT DOCUMENTS

WO    2012166709 A2    12/2012

OTHER PUBLICATIONS

International Search Report and Written Opinion for Application No. PCT/US2014/053186 dated Nov. 17, 2014.

*Primary Examiner* — Alexander Gilman
(74) *Attorney, Agent, or Firm* — Christopher & Weisberg, P.A.

(57) ABSTRACT

A pass-through assembly including a first wall 110d having oppositely-directed inner and outer sides, 112, 114, the first wall 110d defining a first opening 116 extending from the inner side 112 to the outer side 114; an elongated structure 118 extending into the opening 116 from the outer side 114 of the first wall 110d; a first material 130 contacting the first wall 110d and the elongated structure 118 so as to at least partially seal the opening 116, and a second material 140 different from the first material 130, the second material 140 overlying the first material 130 on the outer side 114 of the wall 110d, the second material 140 adhering to the elongated structure 118 and the first wall 110d, the second material 140 having at least one physical property different than a corresponding physical property of the first material 130.

28 Claims, 3 Drawing Sheets

(51) Int. Cl.
    *A61M 1/10* (2006.01)
    *A61M 39/10* (2006.01)
    *A61M 5/142* (2006.01)

(52) U.S. Cl.
    CPC ........ *A61M 1/127* (2013.01); *A61M 39/1011* (2013.01); *A61M 5/14276* (2013.01); *A61M 2205/0216* (2013.01); *A61M 2205/04* (2013.01); *A61M 2210/125* (2013.01)

(58) Field of Classification Search
    USPC ................ 439/271, 589, 606; 174/653, 152; 607/37
    See application file for complete search history.

(56) References Cited

U.S. PATENT DOCUMENTS

| | | | | |
|---|---|---|---|---|
| 2002/0165588 | A1* | 11/2002 | Fraley | A61N 1/3754 607/37 |
| 2005/0092507 | A1* | 5/2005 | Marshall | A61N 1/3754 174/50.59 |
| 2007/0239222 | A1* | 10/2007 | Sprain | A61N 1/3754 607/37 |
| 2010/0121438 | A1* | 5/2010 | Jarvik | A61M 1/101 623/3.13 |

* cited by examiner

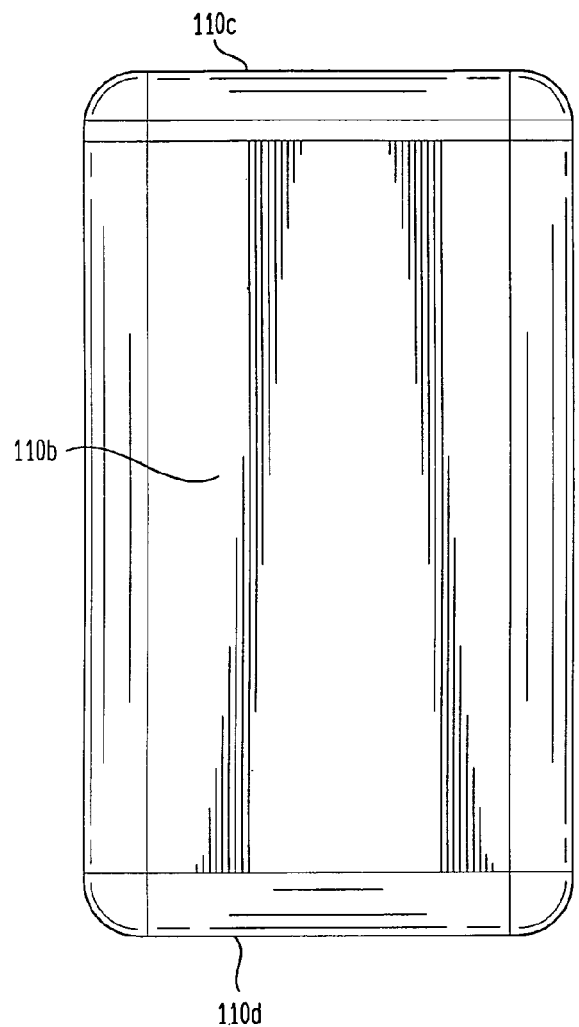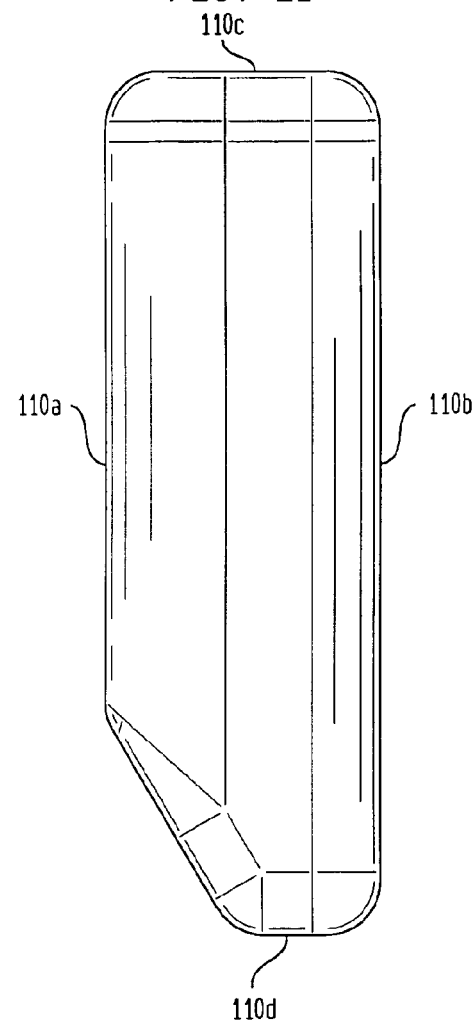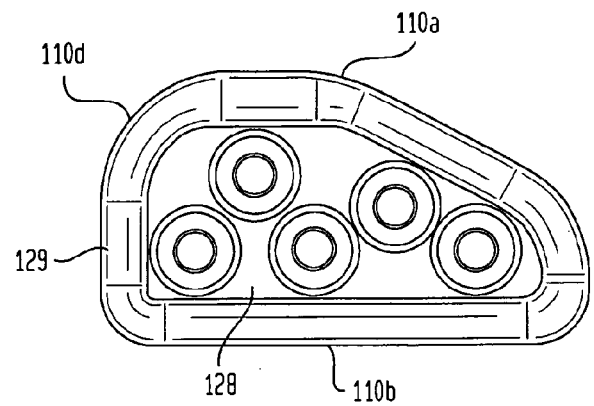

PASS-THROUGH ASSEMBLY

CROSS-REFERENCE TO RELATED APPLICATIONS

The present application is a national phase entry under 35 U.S.C. §371 of International Application No. PCT/US2014/053186, filed Aug. 28, 2014, which claims the benefit of the filing date of U.S. Provisional Patent Application No. 61/871,046 filed Aug. 28, 2013, the disclosures of which are hereby incorporated herein by reference.

BACKGROUND OF THE INVENTION

With the advancement of surgical techniques and electronic components, there is a greater desire to implant such electronic components within the body of a human or other animal. However, when electronic components are to be implanted, it is important to ensure secure and safe connections among such components. For example, an implantable electronic component may be mounted within a housing and connected to a remote component by an elongated structure such as wire or cable extending through a wall of the housing. The arrangement of an elongated structure extending through the wall is commonly referred to as a "pass-through." The pass-through is intended to provide a fluid-tight seal around the elongated structure and, in some cases, should also hold the fluid-tight structure in place relative to the wall of the housing. Moreover, a pass-through used in an implantable housing ordinarily should be biocompatible.

BRIEF SUMMARY OF THE INVENTION

One aspect of the invention provides pass-through assembly. An assembly according to this aspect of the invention desirably includes a first wall having oppositely-directed inner and outer sides. The first wall may define a first opening extending from the inner side to the outer side. The assembly desirably also includes an elongated structure extending into the opening from the outer side of the first wall, and a first material contacting the first wall and the elongated structure so as to at least partially seal the opening. The assembly also may include a second material different from the first material, the second material overlying the first material on the outer side of the wall, the second material adhering to the elongated structure and the first wall.

The second material may one or more have physical properties different from those of the first material. For example, the second material may have an elastic modulus, tensile strength, toughness or adhesion greater than the corresponding property of the first material. Merely by way of example, the first material may be a relatively soft sealant such as a silicon, for example, a biocompatible silicon or a room temperature vulcanizing ("RTV") silicone, whereas the second material may be a material such as an epoxy which forms a secure attachment between the elongated structure and the wall. Moreover, the second material may have greater biocompatibility than the first material.

A further aspect of the invention provides methods of sealing an opening defined in a first wall of a housing. A method according to this aspect of the invention desirably includes: advancing an elongated structure through the opening; applying a first material to the first wall, the first material surrounding the elongated structure; and applying a second material atop the first material, the second material surrounding the elongated structure.

BRIEF DESCRIPTION OF THE DRAWINGS

FIGS. 2A-2C are plan views of the housing assembly of FIG. 1;

DETAILED DESCRIPTION

Figure 1:
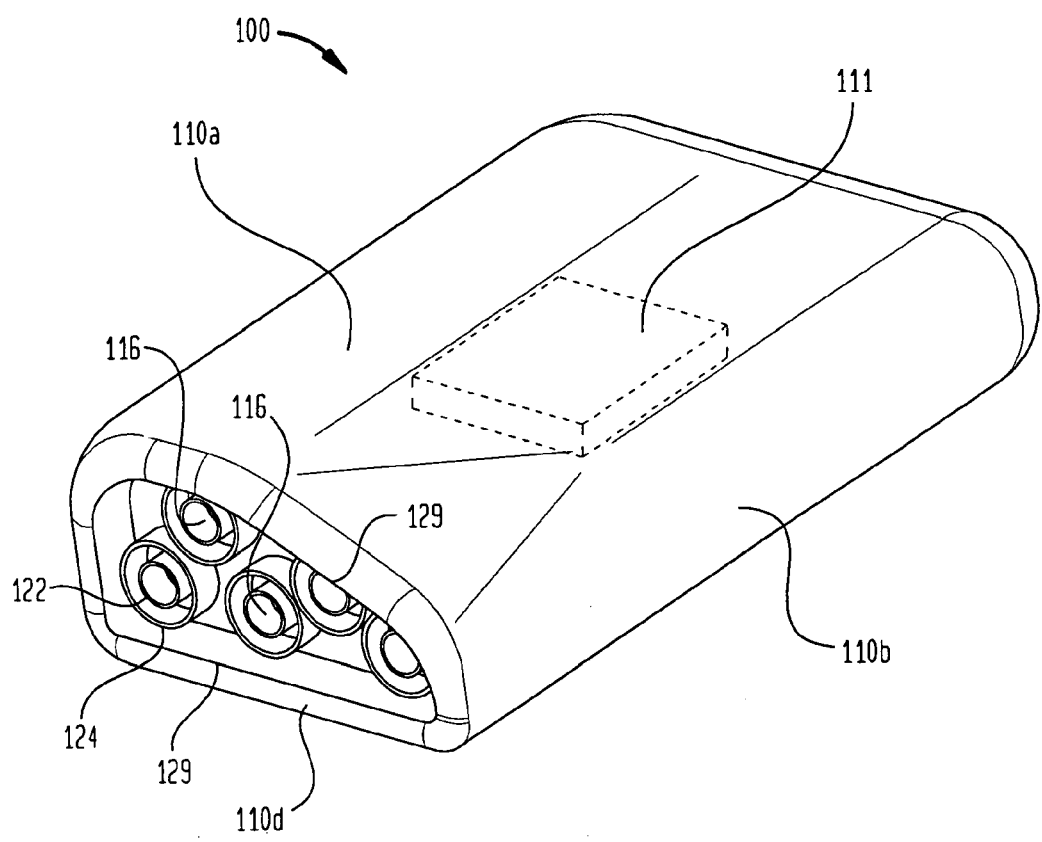
FIG. 1 is a perspective view of a housing assembly according to one embodiment of the invention with certain elements omitted for clarity of illustration.

FIG. 1 is a perspective view of an implantable housing assembly 100 according to one aspect of the disclosure. The housing assembly 100 may be any shape, and in one example may have a generally rectangular shape from a plan view, with or without rounded edges, as shown in the plan view of FIGS. 2A-C. The housing assembly 100 may have a plurality of walls 110a-d that may define a partially or completely enclosed area therebetween. Stated another way, a first wall 110d, together with additional walls 110a-110c cooperatively define a partially or completely enclosed interior space. Any of the walls 110a-d may be integrally formed with one another, or may be detachably secured to one or more of the other walls 110a-d.

Figure 3A:
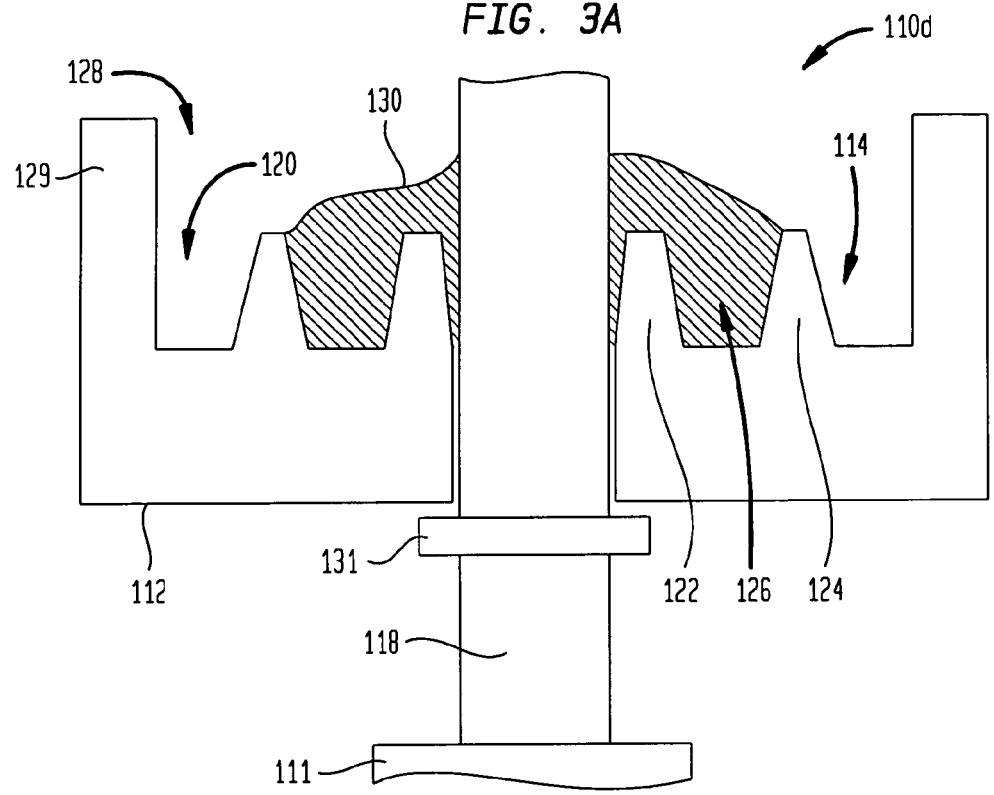
FIG. 3A is a fragmentary cross-sectional view of the housing of FIGS. 1-2C at a stage of a manufacturing process.

As shown in FIGS. 2C and 3A, a wall 110d of the housing assembly 100 may have an inner side 112 and an outer side 114. Portions of the inner side 112 may be substantially flat. Wall 110d may define at least one opening 116 extending entirely through the wall from the inner side 112 to the outer side 114. The opening 116 may be generally cylindrical, or may be any other shape to accommodate an elongate structure 118 discussed further below.

The outer side 114 may define a recess 128 between ridges 129 of the housing assembly. Ridges 129 may be integral with wall 110d or may be defined by other walls of the housing. A base portion 120 forms a floor of the recess facing outwardly. The outer side may have at least one inner ring 122 around the opening 116, and at least one outer ring 124 around the inner ring 122. These rings project in outwardly from the base (toward the top of the drawings in FIG. 3A), such that an annular space 126 is formed between the inner ring and the outer ring. In the particular embodiment depicted, rings 124 and 122 are tapered in the outward direction, away from base 120. Thus, the inner ring 122 defines a conical lead entrance to the opening 116. The base portion 120, rings 122, 124, and annular space 126 may be disposed within the recess 128 between the ridges 129, such that the rings 122 and 124 extend outwardly from the base portion 120 but do not extend outside the recess 128 or past the ridges 129.

The wall 110d may be assembled to the other of the walls 110 to define a partially or completely enclosed area. In one example, electronic components, schematically depicted at 111, may be stored therein. Such electronic components may be, for example, components for the operation of an implantable medical device, such as an implantable ventricular assist device, an implantable battery, or an implantable transcutaneous energy transfer system.

The elongated structure 118 extending though hole 116 may be a flexible wire or electrical cable that may be connected to electronic components 111 within the housing assembly 100. Typically, the opposite end of elongated structure (not shown) is connected to other electronic components (not shown) either implanted within the body or positioned outside the body.

In an assembly process according to one aspect of the invention, one or more elongate structures 118 are inserted through the openings 116. A first material 130 may be applied to outer side 114. For example, as shown in FIG. 3C, the first material 130 may be applied to an exterior portion of the elongate structure 118, atop the inner ring 122, and at least partially within the annular space 126. The first material 130 may also be applied at least partially within the opening 116 itself. In the embodiment shown in FIGS. 3A and 3B, the first material does not extend beyond the outer ring 124.

The first material 130 may at least partially seal the opening 116 when the elongate structure 118 is disposed therein. The first material optionally may form a physical bond with the wall of the elongated structure 118, with the portions of wall 110d defining opening 116, or both. The first material may be a silicone and has a first elastic modulus.

Figure 3B:
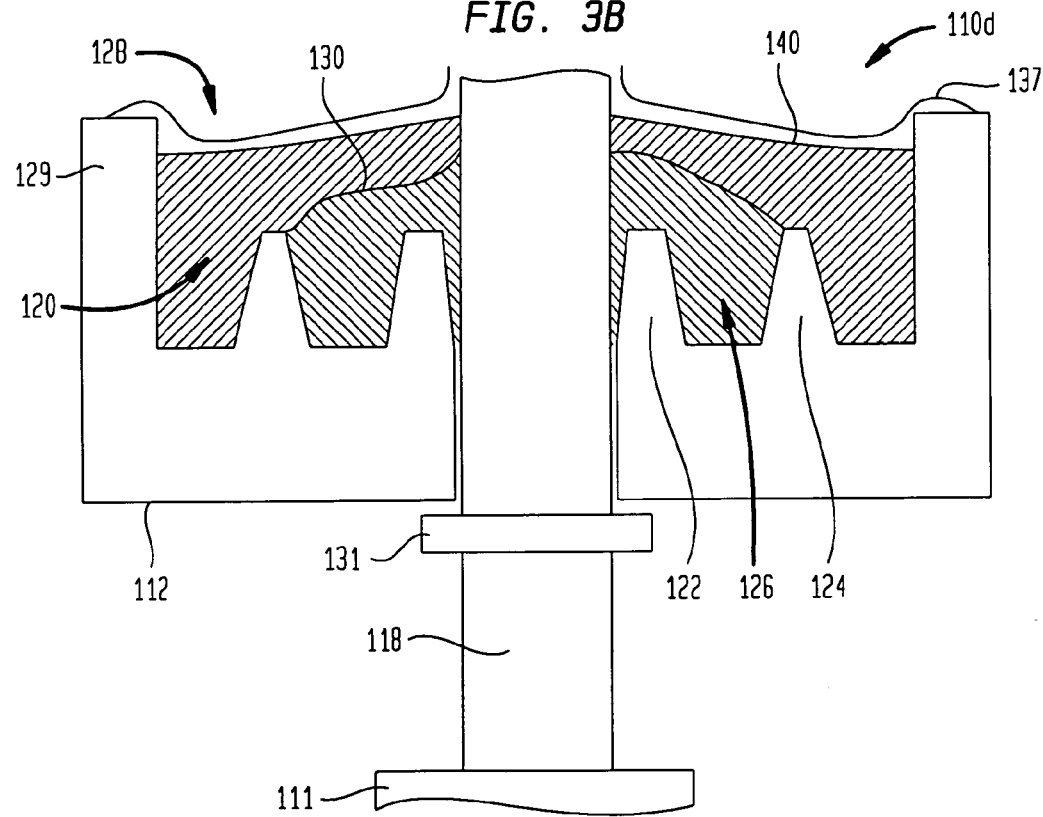
FIG. 3B is a view similar to FIG. 3A depicting the housing assembly of FIGS. 1-3A in a completed state.

Although only one hole is depicted in FIGS. 3A and 3B, elongated structures and first material desirably are provided for the other holes in the same manner.

A second material 140 may be applied atop the first material. The second material 140 may partially or completely cover the first material 130 within the recess 128. In one example, the second material 140 may at least partially, but not completely, fill the recess 128 as depicted in FIG. 3B. For example, a single continuous mass or layer of second material may cover the first material at all of the openings 116. In other examples, discrete portions of the second material are proved at each opening 116. The second material 140 may contact each of the elongated structures and also may contact the wall 110d as, for example, at the base portion 120. The second material also may contact other walls of the housing. The second material 140 may form a bond with the outer surfaces of the elongated elements and with at least one wall of the housing.

Typically, both the first material and the second material are applied in a flowable condition, such as in a liquid, gel or paste-like state. One or both of the materials may be cured to a solid state after application. The curing process may involve a chemical reaction. The conditions required for curing will depend on the compositions of the materials. The curing processes may be performed sequentially, so that the first material is cured before the second material is applied, or simultaneously. Application of the first and second materials desirably takes place after insertion of elongated elements 118 through the openings 116, and may occur before or after the elongated elements are connected to the electronic components 111.

The second material may be different from the first material. For example, the second material may be an epoxy. The second material may have a second elastic modulus. In one example, the second elastic modulus may be different from the first elastic modulus. For example, the second elastic modulus may be greater than the first elastic modulus such that the second material is stiffer than the first material. Alternatively or additionally, the second material may have greater adhesion than the first material to the walls of the housing, to the elongated structures, or both. Also, the second material may have greater biocompatibility than the first material.

This configuration provides a secure interface at the opening 116. In particular, the first material may be selected to provide an effective seal around the elongated components, whereas the second material may be selected to provide a secure physical attachment between the elongated elements and the wall. Moreover, the second material may have a greater degree of biocompatibility than the first material. This allows the use of a first material which provides an effective seal but may not have the desired degree of biocompatibility. The pass-through assembly limits the localized, concentrated stress and/or strain that may be placed on the elongate structure 118 while it is disposed within the opening 116. Limiting of the stress and/or strain may prevent damage to the elongate structure 118 while it is implanted within the body of a mammal and may also prevent the elongate structure 118 from becoming disengaged with the opening 116 of the wall 110d.

In some embodiments, these force limiting effects of the present invention may be further supported by attachment of an at least one ring element 131 to the exterior surface of elongated structure 118, as shown in FIGS. 3A-B. At least one ring element 131 may be a rigid element with an outer diameter greater than the outer diameter of opening 114 so as to require one-way insertion of the flexible structure therein. Alternatively, the at least one ring element 131 may be deformable to permit insertion through opening 114 in an insertion direction, yet non-deformable, or at least rigid enough, to provide a redundant means of resisting the stress and/or strains when elongated structure 118 is advanced in a removal direction. Although depicted in FIGS. 3A-B as flat, ring element 131 may assume alternate shapes, for example, ring element 131 may have a curvilinear surface area with a triangular profile oriented for insertion into opening 116.

In a further variant, a third material may be applied to wall 110d, and desirably to the entire housing assembly 110, after application of the second material. In one example, the third material is a biocompatible material in the form of a coating as schematically depicted at 137. In this example, the third material covers the second material. The third material may be selected primarily for its biocompatibility, rather than for physical properties.

In the embodiments discussed above, the elongated structures 118 are wires or cables. However, other elongated structures such as tubes, rods or the like may be used. The pass-through assemblies can form secure attachments and seals even with flexible elongated elements which may pose difficulties with ordinary sealing and attachment techniques.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:
1. A pass-through assembly comprising:
a first wall having oppositely-directed inner and outer sides, the first wall defining a first opening extending from the inner side to the outer side;
at least one ring disposed around the opening;
an elongated structure extending into the opening from the outer side of the first wall;
a first material contacting the at least one ring, the first wall, and the elongated structure so as to at least partially seal the opening, and a second material overlying the first material on the outer side of the wall and adhering to the elongated structure and the first wall, wherein the second material has at least one physical property different than a corresponding physical property of the first material, at least the second material being a biocompatible material.

2. The pass-through assembly of claim 1, wherein the elongated structure is flexible.

3. The pass-through assembly of claim 2, wherein the first wall has one or more additional openings extending from the inner side to the outer side, the assembly further comprising one or more additional elongated flexible structures extending into the additional openings from the outer side of the first wall.

4. The pass-through assembly of claim 1, wherein the second material covers the first material so that no portion of the first material is exposed at the outer side of the first wall.

5. The pass-through assembly of claim 1, wherein the outer side of the first wall has a base portion and an inner ring projecting outwardly from the base portion around the opening and an outer ring projecting outwardly from the base portion around the inner ring so that the inner and outer rings define an annular space therebetween.

6. A housing assembly comprising a pass-through assembly as claimed in claim 1 and one or more additional walls, the additional walls and the first wall cooperatively defining an interior space, the inner side of the first wall facing inwardly toward the interior space.

7. The housing assembly of claim 6, further comprising a component mounted within the interior space, the elongated structure extending through the first opening into the interior space to the component.

8. A pass-through assembly comprising:
a first wall having oppositely-directed inner and outer sides, the first wall defining a first opening extending from the inner side to the outer side, the outer side having a base portion and an inner ring projecting outwardly from the base portion around the opening and an outer ring projecting outwardly from the base portion around the inner ring so that the inner and outer rings define an annular space therebetween;
an elongated structure extending into the opening from the outer side of the first wall;
a first material contacting the first wall and the elongated structure so as to at least partially seal the opening, wherein the first material is disposed at least partially within the annular space; and
a second material overlying the first material on the outer side of the wall and adhering to the elongated structure and the first wall, the second material having at least one physical property different than a corresponding physical property of the first material.

9. The pass-through assembly of claim 8, wherein the first wall defines a recess in the outer side, and wherein the base portion of the first wall forms a floor of the recess.

10. The pass-through assembly of claim 9, wherein the inner and outer rings extend upwardly from the floor of the recess and are disposed completely within the recess.

11. The pass-through assembly of claim 9, wherein the second material is disposed at least partially within the recess.

12. The pass-through assembly of claim 8, wherein the pass-through is implantable within a body of an animal.

13. The pass-through assembly of claim 12, further comprising:
a third material disposed at least atop the second material, the third material being biocompatible.

14. The pass-through assembly of claim 13, wherein the third material is disposed atop a surface of the housing.

15. The pass-through assembly of claim 8, wherein the first material is a silicone.

16. The pass-through assembly of claim 8, wherein the second material is an epoxy.

17. The pass-through assembly of claim 16, wherein the second material is biocompatible.

18. The pass-through assembly of claim 8, wherein the elongated structure has at least one ring element with an outer diameter greater than the outer diameter of the opening in the first wall.

19. The pass-through assembly of claim 18, wherein the at least one ring element is deformable to permit insertion into the opening in an insertion direction.

20. The housing assembly of claim 8, wherein the elongated structure is an electrical cable.

21. The housing assembly of claim 20, wherein the component is at least one of: an implantable battery, an implantable heart pump, and an implantable transcutaneous energy transfer system.

22. A method of sealing an opening defined in a first wall of a housing, the method comprising:
(a) advancing an elongated structure through the opening and at least one ring disposed around the opening;
(b) applying a first material to the first wall, the first material contacting the at least one ring, surrounding the elongated structure and having a first elastic modulus; and
(c) applying a second material atop the first material, the second material surrounding the elongated structure and having a second elastic modulus.

23. The method of claim 22, further comprising attaching the first wall to one or more other walls of the housing.

24. The method of claim 23, further comprising:
after step (a), connecting a first end of the elongated structure to a component disposed within the housing.

25. The method of claim 22, wherein step (b) further comprises:
applying the first material at least partially within an annular space defined by a base portion of the first wall and a plurality of rings projecting outwardly from the base portion around the opening.

26. The method of claim 25, wherein the plurality of rings are at least partially disposed within a recess defined by the first wall.

27. The method of claim 26, wherein step (c) further comprises:
applying the second material at least partially within the recess.

28. The method of claim 22, further comprising:
(d) applying a third material atop the second material and a surface of the housing, the third material being biocompatible.

* * * * *